(12) United States Patent
Tanaka

(10) Patent No.: US 11,672,499 B2
(45) Date of Patent: Jun. 13, 2023

(54) X-RAY IMAGING APPARATUS AND METHOD OF X-RAY IMAGE ANALYSIS

(71) Applicant: SHIMADZU CORPORATION, Kyoto (JP)

(72) Inventor: Fumiaki Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 375 days.

(21) Appl. No.: 15/874,389

(22) Filed: Jan. 18, 2018

(65) Prior Publication Data

US 2018/0214109 A1 Aug. 2, 2018

(30) Foreign Application Priority Data

Jan. 31, 2017 (JP) .............................. JP2017-016043

(51) Int. Cl.
*A61B 6/00* (2006.01)
*A61B 5/00* (2006.01)

(52) U.S. Cl.
CPC ............ *A61B 6/5217* (2013.01); *A61B 6/481* (2013.01); *A61B 6/507* (2013.01); *A61B 5/4848* (2013.01);
(Continued)

(58) Field of Classification Search
CPC ....... A61B 6/5217; A61B 6/481; A61B 6/507; A61B 6/5205; A61B 6/4233; A61B 5/4848; A61B 6/40; A61B 6/4411; A61B 6/504; G06T 7/0012; G06T 7/20; G06T 7/73; G06T 7/246; G06T 2207/30021; G06T 2207/20101; G06T 2207/30048;
(Continued)

(56) References Cited

U.S. PATENT DOCUMENTS 6,471,656 B1 * 10/2002 Shalman .............. A61B 5/0215
600/486
7,415,169 B2 8/2008 Florent et al.
(Continued)

FOREIGN PATENT DOCUMENTS

CN  102793547 A  11/2012
JP  2004321390  11/2004
(Continued)

OTHER PUBLICATIONS

JP 2017-016043, Notice of Reasons for Refusal, dated dated May 27, 2020, 5 pages—English, 4 pages—Japanese.
(Continued)

*Primary Examiner* — Patricia J Park
*Assistant Examiner* — Adil Partap S Virk
(74) *Attorney, Agent, or Firm* — Andrew F. Young, Esq.; Nolte Lackenbach Siegel

(57) ABSTRACT

An X-ray imaging apparatus includes an X-ray irradiation element, an X-ray detection element, an X-ray image generation element, and an image processing analysis element. The image processing analysis element reflects the analysis point on each frame based on a respective relative location between a characteristic point 10 of the X-ray image consisting of a plurality of frames. In addition, an image analysis element analyzes the time-course variation of the blood flow in the blood vessel of the heart based on the variation of the pixel value at the analysis point of each frame of the X-ray image.

8 Claims, 10 Drawing Sheets

(52) U.S. Cl.
CPC .............. *A61B 6/40* (2013.01); *A61B 6/4233* (2013.01); *A61B 6/5205* (2013.01)

(58) Field of Classification Search
CPC ........... G06T 2207/10116; G06T 2207/30104; A61M 25/104
See application file for complete search history.

(56) References Cited

U.S. PATENT DOCUMENTS

| | | | |
|---|---|---|---|
| 7,991,453 B2 | 8/2011 | Florent et al. | |
| 8,594,271 B2 | 11/2013 | Sakaguchi et al. | |
| 9,230,323 B2 | 1/2016 | Kobayashi et al. | |
| 9,259,199 B2 | 2/2016 | Yao et al. | |
| 9,532,754 B2 | 1/2017 | Sakaguchi et al. | |
| 10,980,498 B2* | 4/2021 | Sato .................. | A61B 6/487 |
| 2002/0173724 A1 | 11/2002 | Dorando ............ | A61B 5/0215 |
| | | | 600/486 |
| 2003/0163052 A1* | 8/2003 | Mott .................. | A61B 5/0215 |
| | | | 600/486 |
| 2005/0002546 A1* | 1/2005 | Florent .............. | G06T 5/50 |
| | | | 382/128 |
| 2005/0107688 A1* | 5/2005 | Strommer .......... | A61F 2/95 |
| | | | 600/424 |
| 2006/0058643 A1* | 3/2006 | Florent ............. | G06T 7/38 |
| | | | 600/423 |
| 2006/0173292 A1* | 8/2006 | Baba ................. | A61B 8/469 |
| | | | 600/425 |
| 2008/0045827 A1* | 2/2008 | Rongen ............. | A61B 6/504 |
| | | | 600/407 |
| 2009/0169080 A1* | 7/2009 | Noordhoek ........ | G06T 5/003 |
| | | | 382/131 |
| 2010/0142792 A1* | 6/2010 | Sakaguchi ......... | A61B 6/00 |
| | | | 382/132 |
| 2010/0234698 A1* | 9/2010 | Manstrom .......... | A61M 5/007 |
| | | | 600/301 |
| 2010/0298705 A1* | 11/2010 | Pelissier ............ | A61B 8/4254 |
| | | | 600/443 |
| 2012/0300903 A1 | 11/2012 | Yao et al. | |
| 2015/0042677 A1* | 2/2015 | Shimamura ......... | A61B 6/469 |
| | | | 345/632 |
| 2015/0154771 A1* | 6/2015 | Sakaguchi .......... | A61B 6/12 |
| | | | 345/443 |
| 2015/0161790 A1* | 6/2015 | Takahashi .......... | G06T 7/0016 |
| | | | 600/424 |
| 2015/0262357 A1* | 9/2015 | Igarashi ............. | G06T 7/0016 |
| | | | 382/131 |
| 2016/0029989 A1* | 2/2016 | Nagae ............... | A61B 6/12 |
| | | | 378/42 |
| 2016/0066795 A1* | 3/2016 | Grass ................ | A61B 5/02007 |
| | | | 600/407 |
| 2016/0089097 A1* | 3/2016 | Ohishi ............... | G09G 5/026 |
| | | | 378/62 |
| 2016/0143605 A1* | 5/2016 | Nagae ............... | A61B 6/5211 |
| | | | 378/62 |
| 2016/0196666 A1* | 7/2016 | Venkatraghavan ... | G06T 7/254 |
| | | | 382/130 |
| 2016/0350913 A1* | 12/2016 | Nagae ............... | A61B 6/487 |
| 2017/0065235 A1 | 3/2017 | Sakaguchi et al. | |
| 2017/0119332 A1* | 5/2017 | Takaya .............. | A61B 6/4441 |
| 2017/0323440 A1* | 11/2017 | Tsunomori ......... | G06T 7/13 |
| 2019/0015056 A1* | 1/2019 | Sato .................. | G06V 10/44 |

FOREIGN PATENT DOCUMENTS

| | | |
|---|---|---|
| JP | 2005-510288 | 4/2005 |
| JP | 2006-506117 | 2/2006 |
| JP | 2010-131371 | 6/2010 |
| JP | 2012245351 | 12/2012 |
| JP | 2015-217170 | 12/2015 |

OTHER PUBLICATIONS

Chinese Pat. Appln. No. 201810053270.7, Office Action dated Nov. 18, 2020, 10 pages—Chinese, 9 pages—English.

* cited by examiner

X-RAY IMAGING APPARATUS AND METHOD OF X-RAY IMAGE ANALYSIS

CROSS REFERENCE TO RELATED APPLICATIONS

This application relates to, and claims priority from JP Ser. No. JP2017-016043, filed Jan. 31, 2017, the entire contents of which are incorporated herein by reference.

FIGURE SELECTED FOR PUBLICATION

FIG. 1

BACKGROUND OF THE INVENTION

Field of the Invention

The present invention relates to an X-ray imaging apparatus and more particularly, relates to an X-ray imaging apparatus and a method of X-ray image analysis under a condition in which an administered contrast agent exists.

Description of the Related Art

Conventionally, an X-ray imaging apparatus that implements imaging under the condition in which an administered contrast agent exists and a method of an X-ray image analysis that is executed thereunder are known. Such X-ray imaging apparatus and a method of an X-ray image analysis are disclosed e.g., in JP2015-217170, the entire contents of which are incorporated herein by reference.

Reference JP2015-217170 discloses an aspect in which a first angiographic image as a difference image between the images taken before the administration of the contrast agent to the subject and under the administration of the contrast agent to the subject is prepared prior to a medical treatment. Then, when a second angiographic image is taken after the medical treatment based on the first angiographic image, a medical doctor himself designates the monitor region to be observed and a time-density curve (TDC) is obtained based on the concentration of the contrast agent in the monitor region. An X-ray irradiation time is determined based on the obtained TDC when the second angiographic image is taken.

In addition, an aspect that calculates such as a rate and an amount of the blood flow from an obtained TDC without using an additional device is disclosed in JP2015-217170. Further, the additional device relative to the specification of the present invention is the device used to implement an examination and measurement applying e.g., A doppler method and a fraction flow reserve (FFR) measurement and so forth.

Unfortunately, it is a given that according to the X-ray imaging apparatus disclosed in the JP2015-217170, each frame of the second angiographic image taken with the administered contrast agent is the image at the same location when the TDC is obtained. Specifically, the image is taken given the blood vessel is still. Accordingly, the location that is imaged relative to a heart that is a region in which the blood vessels thereof are frequently moving is necessarily different depending on each frame, so that it is problematic and hard to comprehend the status of the blood flow from the image with any accuracy. Therefore, according to the JP2015-217170, an operation using an additional device such as a device that executes FFR in the blood vessel is further required to approximately comprehend the status of the blood flow in the region such as a heart where the blood vessel moves. However, in such cases, the number of X-ray irradiations increases when the additional device is carried to the blood vessel of the heart, so that it is further problematic that radiation exposure increases for a patient.

ASPECTS AND SUMMARY OF THE INVENTION

The present invention intends to address at least one of the concerns as set forth above and one of the purposes of the present invention is to provide an X-ray imaging apparatus that allows the operator to comprehend the status of the blood flow in the blood vessel in the X-ray image without using any additional device, and in addition, to cut the operation time and the radiation exposure; and to provide a method of X-ray image analysis therefor.

To achieve the above purpose, an X-ray imaging apparatus according to an optional first aspect of the present invention comprises: an X-ray irradiation element that irradiates an X-ray to a subject; a detection element that detects the X-ray that transmits through the subject; an X-ray image generation element that generates an X-ray image of the subject; and an image processing analysis element that processes the X-ray image of the subject, wherein the image processing analysis element reflects an analysis point based on a relative location of each of a characteristic point of the X-ray image consisting of a plurality of frames that images the subject and an analysis point that is set up based on location data of the characteristic point in each frame, and analyzes a time-course variation in a blood vessel based on a variation of pixel values at an analysis point in each frame of the X-ray image.

The X-ray imaging apparatus according to another optional first aspect of the present invention as set forth above comprises: the X-ray irradiation element; the X-ray detection element; the image generation element; and the image processing analysis element that processes the X-ray image of the subject, wherein the image processing analysis element reflects an analysis point based on a relative location of each of a characteristic point of the X-ray image consisting of a plurality of frames that images the subject land an analysis point that is set up based on location data of the characteristic point in each frame, and analyzes a time-course variation in a blood vessel based on a variation of pixel values at an analysis point in each frame of the X-ray image.

Accordingly, even when the location of the blood vessel changes in between each frame of the X-ray image of the subject, the analysis point of each frame can be set up on the basis of the characteristic point that moves along with the blood vessel, so that the time-course variation of the blood flow in the blood vessel from the X-ray image can be analyzed. Consequently, the operator can comprehend the status of the blood flow in the blood vessel in the X-ray image without using any additional device even relative to the region, such as a heart, where the blood vessel moves, and in addition, can cut the operation time and the radiation exposure.

Relative to the X-ray imaging apparatus, according to one of the optional aspects as set forth above, preferably, the image processing analysis element further comprises: a characteristic point acquisition element that acquires location data relative to each frame of the X-ray image; an analysis point setting element that sets up the analysis point on the blood vessel in the X-ray image based on the location data of each characteristic point every frame; and an image analysis element that analyzes the time-course variation of the blood flow in the blood vessel based on the variation of the pixel value at the analysis point in each frame of the X-ray image. According to such an aspect, the analysis point on the blood vessel in the X-ray image can be set up, so that the analysis of the time-course variation of the blood flow in the blood vessel can be analyzed in further detail.

Relative to the X-ray imaging apparatus according to the optional first aspect as set forth above, preferably, the image processing analysis element calculates at least one of the blood flow rate at the analysis point and the blood flow amount thereat. According to such aspect, the rate of the blood flow and the amount thereof can be calculated from the X-ray image. Consequently, at least one of the rate of the blood flow and the amount thereof can be calculated without using an additional device such as the device implementing the Doppler method.

Relative to the X-ray imaging apparatus according to one of the alternative first aspects as set forth above, preferably, the image processing analysis element sets up an analysis point at the predetermined location acquired based on the coordinate of the characteristic point. According to such aspect, the analysis point can be automatically set up without an input from a user, the usability can increase.

Relative to the X-ray imaging apparatus according to one of the alternative first aspects as set forth above, preferably, the image processing analysis element further comprises an input receiving element that receives the input from the user, and the image processing analysis element sets up an analysis point in the frame selected by the user based on the input from the user. According to such aspect, the analysis point can be set up by reflecting the intention of the user, so that the analysis can be implemented along with the intention of the user.

Relative to the X-ray imaging apparatus according to one of the alternative first aspects as set forth above, preferably, the image processing analysis element further comprises an input receiving element that receives the input from the user, and the image processing analysis element cuts out each frame of the X-ray image, which is continuously acquired based on the characteristic point, video-outputs the characteristic point images of which location is fixed on the basis of the characteristic point in order, and sets up an analysis point based on the input from the user. According to such aspect, the analysis point can be set up using the video-image, in which the characteristic point displayed in real time without searching a frame that facilitates to make sure the characteristic point, when the analysis point is set up.

Relative to the X-ray imaging apparatus according to one of the alternative first aspects as set forth above, preferably, the image processing analysis element analyzes the blood flow in the blood vessel of the heart. According to such aspect, the blood flow of the heart can be analyzed while beating. As results, even when the blood vessel of the heart is hard to be analyzed due to the vigorous movement thereof, such blood vessel can be analyzed with the X-ray image without using any additional device. Now, the introduction of the additional device into the blood vessel takes more time and increases the radiation exposure. On the other hand, according to the aspect of the present invention, the introduction of such additional device is eliminated, so that the time needed for the operation during a cardiovascular treatment can be cut and the radiation exposure can be effectively reduced.

In such cases, in another alternative aspect of the present invention preferably, the image processing analysis element implements the analysis while a balloon is in place in the blood vessel of the heart. Now, when the additional device is used to analyzes the blood flow, the balloon and the device are exchanged respectively, so that an introduction of each and a removal thereof are needed, but in contrast, no additional device is needed according to the aspect of the present invention. As results, the number of the operation steps can be eliminated.

It is farther optionally preferable that the image processing analysis element analyzes the blood flow respectively before and after the dilation of the blood vessel with the balloon. Now, when the additional device is used, the measurement of the blood flow and the dilation of the blood vessel must be carried out with the additional device and the balloon. Specifically, when the additional device is used, the device applied to FFR (FFR device) is introduced into the narrow region of the blood vessel to measure the blood flow prior to dilation of the blood vessel. The balloon is introduced into the narrow region of the blood vessel to dilate the blood vessel following the removal of the FFR device. The FFR device is reintroduced into the dilated region of the blood vessel to measure the blood flow following the removal of the balloon. When the dilation of the blood vessel is not satisfactory, it is necessary that the FFR device is introduced into the narrow region of the blood vessel to measure the blood flow after the balloon is reintroduced to dilate the blood vessel and then removed therefrom. However, given the blood flow is respectively analyzed before and after the dilation of the blood vessel with the balloon, no additional device is required to be introduced. In addition, for example, even when the blood vessel dilation is unsatisfactory, the dilation of the blood vessel can be carried out again as is. Therefore, the operation time can be cut compared to the case when an additional device is used to analyze the blood flow. In addition, even when the blood vessel is re-dilated, no balloon is required to be re-introduced, so that the number of the X-ray irradiation due to introductions of the balloon can be reduced. As results, the radiation exposure can be cut.

According to another aspect of the present invention, there is provided an X-ray image analysis method according to the second aspect of the present invention comprising the steps of; acquiring location data relative to each frame of characteristic points of an X-ray image consisting of a plurality of the frames imaging a subject; reflecting an analysis point on a blood vessel in the X-ray image on each frame based on each relative location between the characteristic point of each frame and the analysis point that is set-up based on the location data of the characteristic point every frame; and analyzing a time-course variation of a blood flow in a blood vessel based on the variation of an image of the analysis point in each frame of the X-ray image.

The X-ray image analysis method according to the second aspect of the present invention further comprises the steps of: acquiring the location data relative to each frame of characteristic points; reflecting the analysis point on the blood vessel in the X-ray image on each frame; and analyzing the time-course variation of the blood flow in the blood vessel based on the variation of the image of the analysis point of each frame of the X-ray image.

Accordingly, even when the location of the characteristic point varies relative to each frame of the X-ray image of the subject, the analysis point of each frame can be set up by the step of reflecting the analysis point on the blood vessel in the X-ray image on each frame. In addition, the time-course variation of the blood flow in the blood vessel can be analyzed by the step of analyzing the time-course variation of the blood flow in the blood vessel. Consequently, the X-ray image analysis method can be provided, by which the operator can comprehend the status of the blood flow in the blood vessel in the X-ray image without using any additional device even relative to the region, such as a heart, where the blood vessel moves, and in addition, and can cut the operation time and the radiation exposure.

The above and other aspects, features and advantages of the present invention will become apparent from the following description read in conjunction with the accompanying drawings, in which like reference numerals designate the same elements.

EFFECT OF THE INVENTION

According to the aspect of the present invention, the X-ray imaging apparatus and the X-ray image analysis method can be provided, by which the operator can comprehend the status of the blood flow in the blood vessel in the X-ray image without using any additional device even relative to the region, such as a heart, where the blood vessel moves, and in addition, and can cut the operation time and the radiation exposure.

DETAILED DESCRIPTION OF THE PREFERRED EMBODIMENTS

Figure 1:
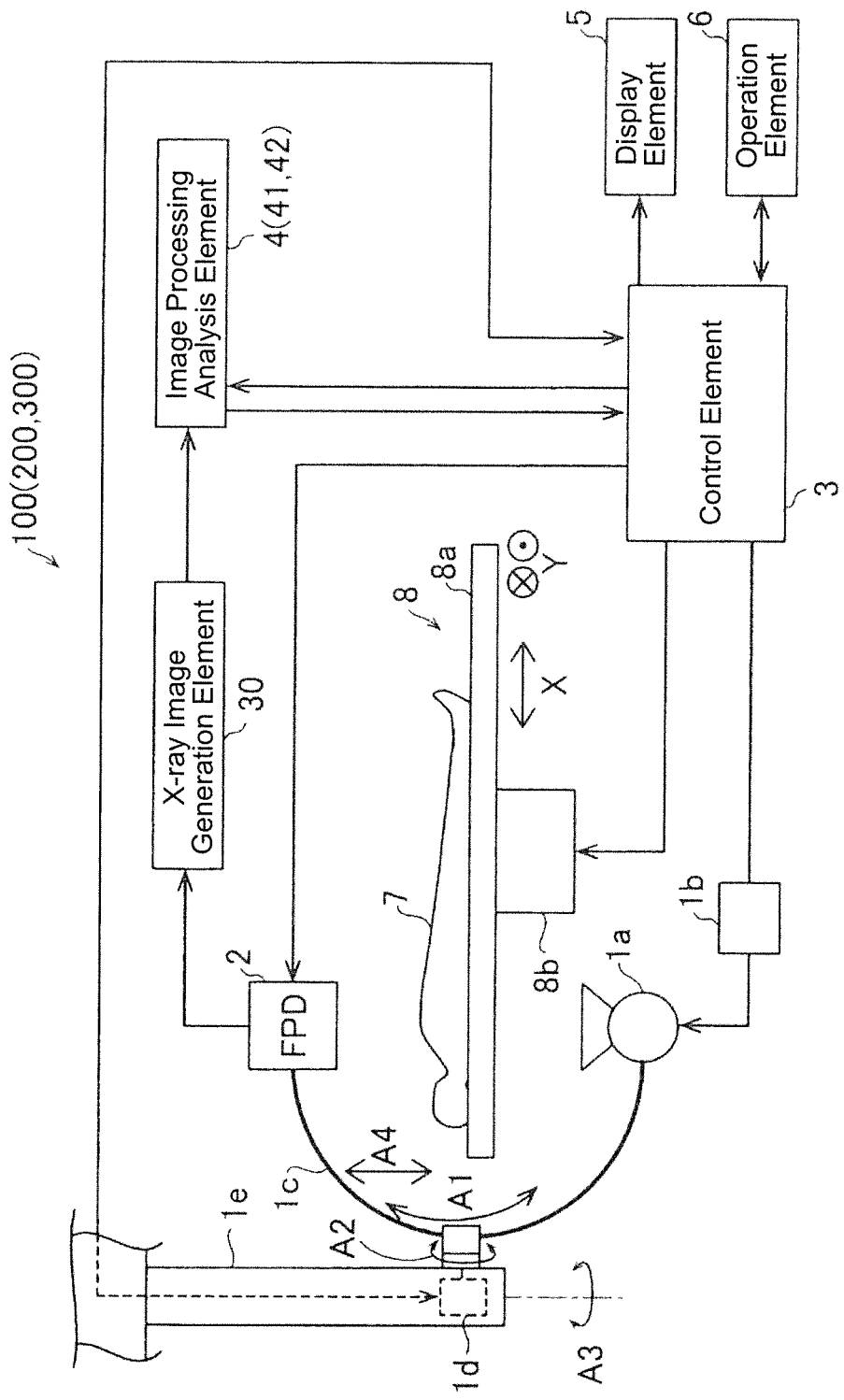
FIG. 1 is a schematic view illustrating an entire structure of an X-ray imaging apparatus according to the aspects of the Embodiments 1-3 of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, a 'computer-based system' comprises an input device for receiving data in any form, an output device for outputting data in any tangible form (e.g. data stream, imaging stream, for processing, printing or displaying etc. on a computer screen), a memory for storing data as well as computer code, and a processor for executing stored computer code wherein said computer code resident in said memory will physically cause said processor to read-in data via said input device, process said data within said microprocessor and output said processed data via said output device. It will be understood that each component also includes any required subcomponents for operation (resistors, capacitors, wires, heat sinks etc.) as will be known to those of skill in the art.

It will be further understood by those of skill in the art that the apparatus and devices and the elements herein, without limitation, and including the sub components such as operational structures, circuits, communication pathways, and related wire and printed elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer related process and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Preferred Aspect of the Embodiment

The inventor, sets forth specific Embodiments of the present invention based on the following FIGS.

Embodiment 1

Referring to FIG. 1 to FIG. 5, the inventor illustrates the system of the X-ray imaging apparatus 100 according to the aspect of the Embodiment 1 of the present invention.

[System of an X-ray Imaging Apparatus]

First, referring to FIG. 1, the inventor sets forth the system of the X-ray imaging apparatus 100 according, to the aspect of the Embodiment 1.

An X-ray imaging apparatus 100 according to the aspect of the Embodiment 1 is, for example, an angiography apparatus to image the blood vessel 7a of a heart of a subject 7 (referring to FIG. 4) under the condition in which a contrast agent is administered into the blood vessel. Now, the subject 7 is a biological body, e.g., a human. And, when an operator introduces a balloon 9 (referring to FIG. 5) into the narrow region 12 (referring to FIG. 5) of the blood vessel of the heart of the subject 7, the contrast agent is administered into the blood vessel 7a of the heart of the subject 7 using a catheter (not shown in FIG.) and then an X-ray image is taken.

Referring to FIG. 1, the X-ray imaging apparatus 100 comprises an X-ray irradiation element 1a, a FPD 2 (flat panel detector), a control element 3, an image processing element 4, a display element 5, an operation element 6, and a loading member 8. In addition, the FPD 2 is an example of a "X-ray detection element' in the claims.

The X-ray irradiation element 1a irradiates a radiation toward the subject 7 (FPD 2) when an X-ray tube driving element 1b adds a voltage thereto.

The FPD 2 detects the X-ray that transmits through the subject 7, converts the detected X-ray to an electric signal, and reads the converted electric signal as an image signal. Then, the FPD 2 that is connected to the X-ray image generation element 30 sends the image signal to the X-ray image generation element 30.

The X-ray image generation element 30 comprises e.g., an CPU (central processing unit). The X-ray image generation element 30 generates the X-ray image of the subject 7 based on the image signal sent from the FPD 2. Then, the X-ray image generation element 30 that is connected to the X-ray image processing analysis element 4 sends the generated X-ray image to an image processing analysis element 4.

Each of the X-ray irradiation element 1a and the FPD 2 is installed to the one end and the other end of the holding member 1c, having C-like shape, as facing to each other and sandwiching the subject 7. In addition, the holding member 1c is hanged from the ceiling with a support member 1e in the room where the X-ray imaging apparatus 100 is in place. In addition, the support member 1e comprises an arm driving member 1d that moves the holding member 1c based on the directive from the control element 3. The arm driving member 1d comprises e.g., a motor and drives the motor based on the directive from the control element 3 to move the support member 1c.

For example, the arm driving member 1d can slide the C-like shaped support member 1c in the arrow A1 direction (direction along the support member 1c), can rotate the support member 1c in the arrow A1 direction and the arrow A3 direction around the predetermined rotation axis, and can move vertically the support member 1c in the arrow direction A4.

The control element 3 comprises e.g., the CPU and transmits a control signal (directive) to the X-ray irradiation element 1a, the FPD and loading member 8. Further, the control element 3 acquires the input-operation data, received from the operator through the operation element 6. Further, the control element 3 transmits the acquired input-operation data to the image processing analysis element 4.

The image processing analysis element 4 comprises e.g., an CPU (central processing unit). The image processing analysis element 4 analyzes the blood flow in the blood vessel 7a of the heart using the X-ray image taking the blood vessel 7a of the heart of the subject 7. The inventor sets forth the detail later.

The display element 5 displays an X-ray image output from the image processing element 4. The display element 5 comprises e.g., a liquid crystal display.

Further, the operation element 6 transmits the input-operation input from the operator to the control element 3 and the image processing analysis element 4. The operation element comprises e.g., a mouse and a keyboard.

The loading member 8 comprises a table 8a on which, the subject 7 can be loaded, and a table driving element 8b that drives the table 8a. The table 8a has e.g., a flat plane (loading plane) on which the supine subject 7 can be loaded. Then, when the subject 7 is subjected to an X-ray imaging, the subject 7 is fixed on the table 8a, and the subject 7 and the table 8a move in a unified manner. The table driving member 8b comprises e.g., a motor and drives the motor based on the directive from the control element 3 to move the table 8a horizontally (X-direction and Y-direction) and vertically (Z-direction).

Figure 2:
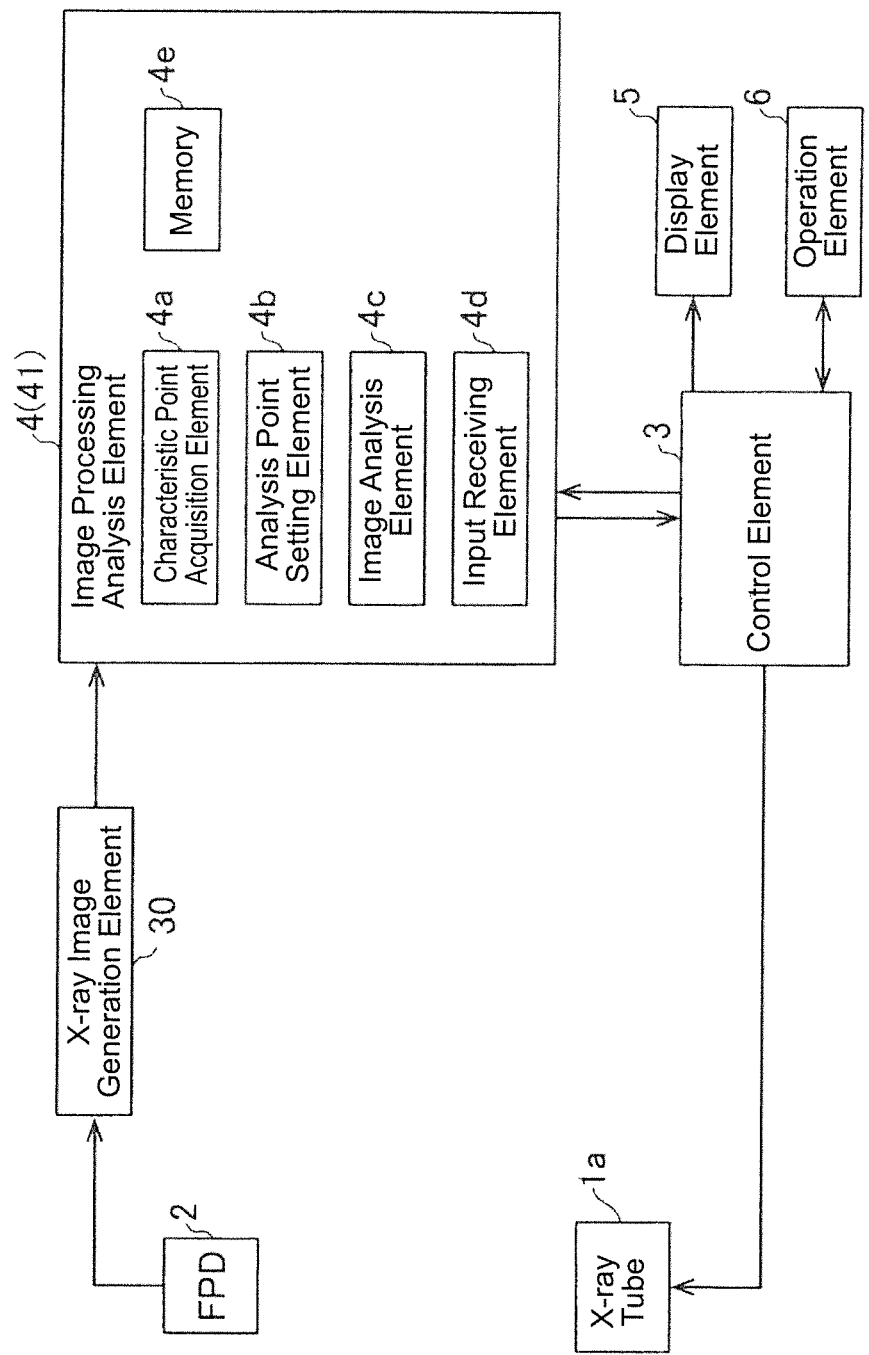
FIG. 2 is a block view illustrating the entire structure of the X-ray imaging apparatus according to the aspects of Embodiment 1, and optionally the Embodiment 2 of the present invention.
Figure 3:
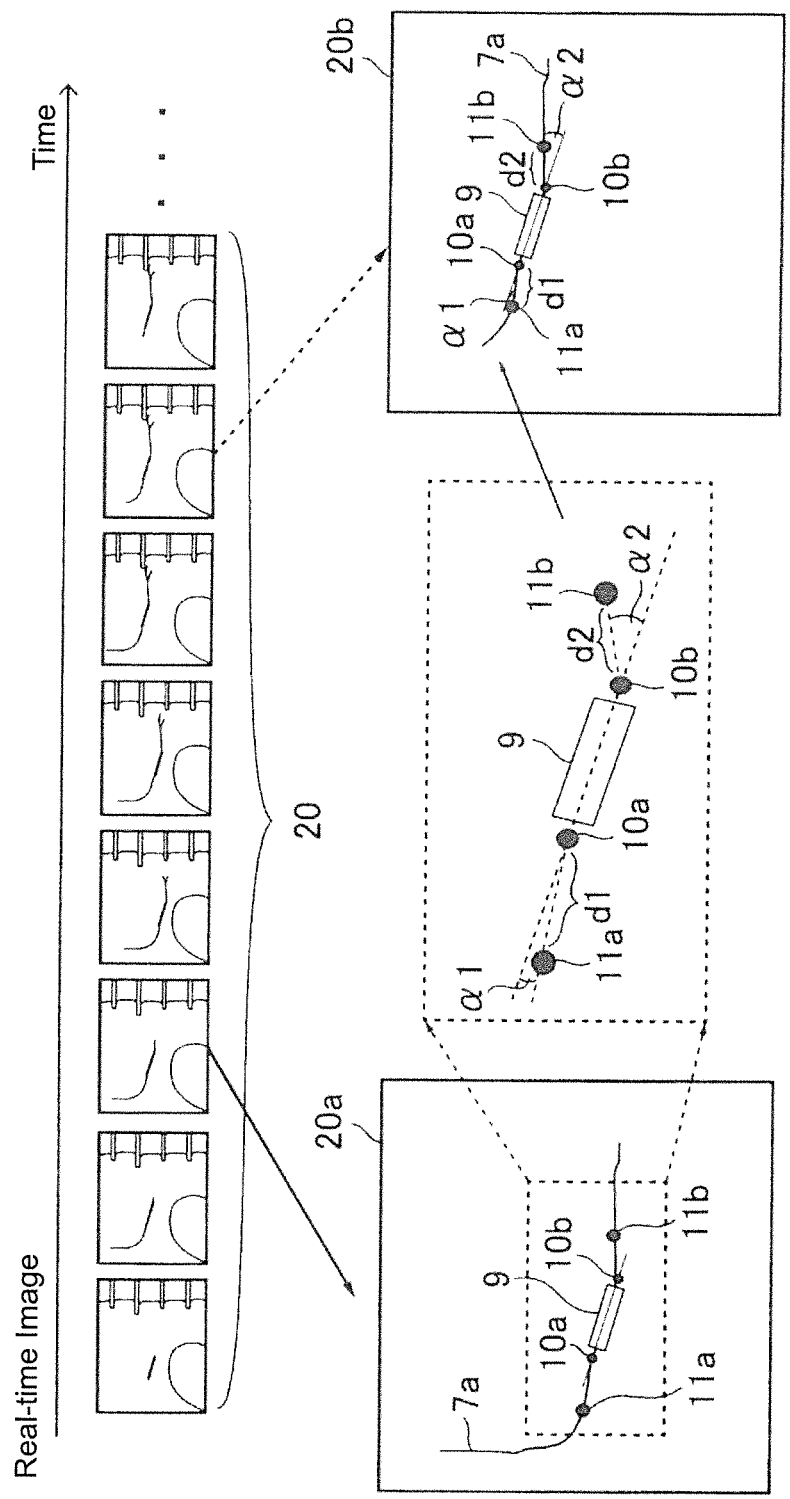
FIG. 3 is a schematic view illustrating a method that sets up the analysis point of the X-ray imaging apparatus according to the aspect of Embodiment 1 of the present invention.
Figure 4:
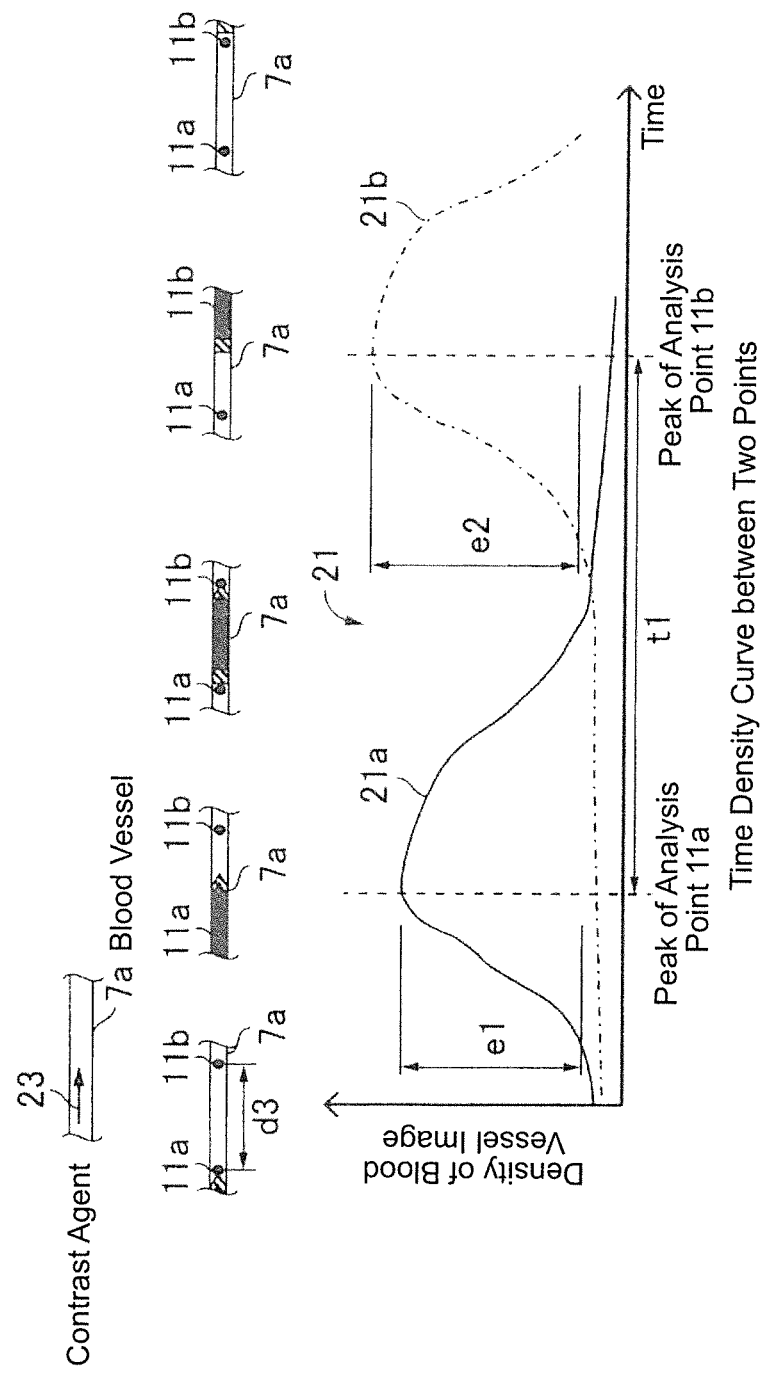
FIG. 4 is a schematic view illustrating a method that analyzes the time-course variation of the blood flow in the blood vessel of the X-ray imaging apparatus according to the aspect of Embodiment 1 of the present invention.

Next, referring to FIG. 2-FIG. 4, the inventor sets forth an image processing method with the image processing analysis element 4.

Referring to FIG. 3, according to the aspect of the Embodiment 1, the image processing analysis element 4 reflects a characteristic point 10 of the X-ray image consisting of a plurality of frames 20 that images the blood vessel 7a of the heart of the subject 7 and an analysis point 11 set up based on location data relative to a characteristic point 10 in each frame 20 on each frame 20, and in addition, analyzes a time-course variation in a blood vessel 7a based on a variation of pixel values in an analysis point 11 at each frame 20 of the X-ray image. In addition, the X-ray image is a video that takes the blood vessel 7a of the heart of the subject 7 at the predetermined frame rate (e.g., 60 fps) and the frame 20 is an image-figure of each frame of the video. Each frame 20 is incorporating the blood vessel 7a of the heart and a balloon 9, and the blood vessel 7a also moves along with the heartbeat, so that the arrangement of the blood vessel 7a of the heart and the balloon 9 is different one another every frame 20. In addition, the characteristic point 10 is a marker installed to the balloon 9.

Referring to FIG. 2, in detail, according to the aspect to the aspect of the Embodiment 1, the image processing analysis element 4 comprises a characteristic point acquisition element 4a, an analysis setting element 4b, an image analysis element 4c, an input receiving element 4d, and a non-volatile memory 4e. The characteristic point acquisition element 4a acquires location data of the characteristic point 10 referring to FIG. 3) relative to each frame 20 (referring to FIG. 3) relative to each frame 20 (referring to FIG. 3) of the X-ray image. In addition, an analysis point setting element 4b sets up the analysis point 11 on the blood vessel 7a of the heart in the X-ray image based on the location data of each characteristic point 10 of every frame 20. In addition, an image analysis element 4c analyzes the time-course variation of the blood flow 7a in the blood vessel of the heart based on the variation of the pixel value of the analysis point 11 of each frame of the X-ray image.

According to the aspect of the Embodiment 1, the image processing analysis element 4 calculates the rate of the blood flow running through the analysis point 11 as the time-course variation of the blood flow in the blood vessel 7a of the heart. In addition, the image processing analysis element 4 calculates the flow amount of the blood flow running through the analysis point 11. In addition, the input receiving element 4d receives the input from a user (operator). The memory 4e stores the acquired video images and so forth. Further, referring to FIG. 2, it illustrates the aspect of the image processing analysis element 4 is achieved with a single CPU, but an individual CPU can make each element from a function to a function.

The location data of the characteristic point 10 is the coordinate of the characteristic point 10 in the X-ray image. In addition, the analysis point 11 is an area consisting of a plurality of pixels set up in the X-ray image, and is denoted as a point (analysis points 11a, 11b) in the X-ray image. In addition, according to the aspect of the Embodiment 1, the analysis points 11 are set up at two locations of the analysis points 11a and 11b. Further, an acquisition method of the characteristic point 10 is disclosed in the JP2015-510288, in which a marker is extracted from an X-ray image and the location data of the marker is acquired, and even for the present Embodiment, the location data of the characteristic point 10 can be acquired using the same method, so that an explanation is not provided. In addition, the method other than disclosed in JP2005-510288 can be applied to acquisition.

Referring to FIG. 3, real-time images of X-ray images obtained when the balloon 9 having the characteristic point 10 in the blood vessel 7a of the heart of the subject 7 is introduced and the contrast agent is administered through the catheter are illustrated. Referring to FIG. 3, the image processing analysis element 4 sets up an analysis point 11 in the frame 20a selected by the user from each frame 20a based on the input from the user.

In detail, the user selects the frame 20a in which the characteristic point 10 can be easily confirmed and selects the location by using a mouse and so forth, at which the analysis point 11 in the X-ray image is desirably set up. The input receiving element 4d receives the location of the analysis point 11 that is input from the user, and such location is stored in the memory 4e.

In addition, the characteristic point acquisition element 4a sends the location data of the characteristic point 10 in each frame 20 to the memory 4e, and the location data of the characteristic point 10 in each frame is stored in the memory 4e.

Next, the analysis point setting element 4b acquires the relative location data between the analysis point 11 and the characteristic point 10 based on the analysis point 11 that the input receiving element 4d acquires relative to the frame 20a. For example, the analysis point setting element 4b acquires the angle α1 and the distance D1 between the characteristic point 10a and the analysis point 11a, and the angle α2 and the distance D2 between the characteristic point 10b and the analysis point 11b. Then, the analysis point setting element 4b sets up the analysis point 11 of each frame 20 from the acquired relative location data and the location data that is stored in the memory 4e as to the characteristic point 10 in each frame 20, Further, referring to FIG. 3, an example, in which the analysis point 11 is set up relative to the other frame 20b which is different from the frame 20a among the plurality of the frames 20, is illustrated. Accordingly, the image processing analysis element 4 sets up an analysis point 11 based on the location data of the characteristic point and the acquired relative location data.

Next, referring to FIG. 4, the inventor sets forth the analysis method of the time-course variation of the blood flow in the blood vessel 7a of the heart at the analysis point 11. FIG. 4 is the schematic view illustrating the aspect of which the contrast agent is running in the blood vessel 7a of the heart, wherein the vertical axis represents the concentration of the contrast agent (density of the blood vessel image) and the horizontal axis represents the time-course in the graph 21 (time-density curve). The density of the contrast agent is the pixel value in the X-ray image. Referring to FIG. 4, an example is illustrating that the contrast agent administered into the blood vessel 7a of the heart is carried and runs in the blood from the analysis point 11a to the analysis point 11b as indicated by the arrow 23. The graph 21a is a graph illustrating the time-course variation of the blood vessel image of the analysis point 11a, and the 21b is a graph illustrating the time-course variation of the blood vessel image (pixel values) of the analysis point 11b. The peak time of the blood vessel image (pixel values) of the analysis point 11a and the analysis point 11b can be obtained from such graphs. Then, the blood flow rate running in the blood vessel between the analysis point 11a and the analysis point 11b can be obtained from the distance d3 between the analysis point 11a and the analysis point 11b and the time-difference t1 between peaks at which each density of the blood vessel images becomes highest (the peak). In addition, the blood flow amount at the analysis point 11a can be calculated from the difference e1 between the point at which the density (pixel values) of the blood vessel image begins to increase and the maximum value of the density (pixel values) of the blood vessel image. In addition, the blood flow amount at the analysis point 11b can be calculated from the difference e2 between the point at which the density (pixel values) of the blood vessel image begins to increase and the maximum value of the density (pixel values) of the blood vessel image.

Figure 5:
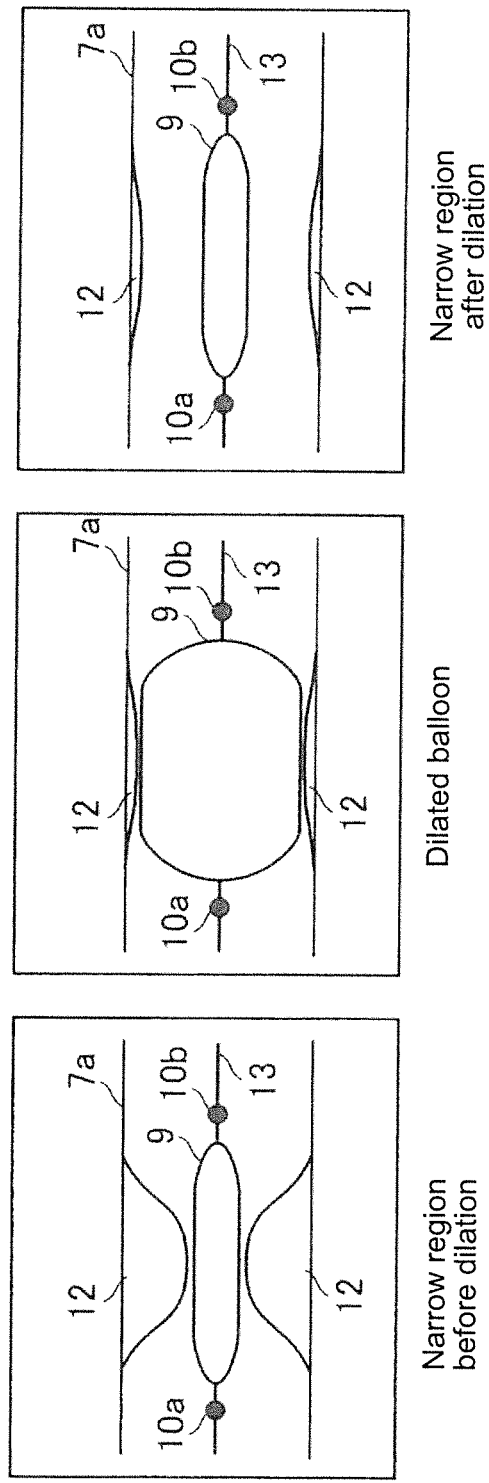
FIG. 5A, FIG. 5B, FIG. 5C are schematic image views illustrating the narrow region at each state, i.e., before a balloon dilation in FIG. 5A of the X-ray imaging apparatus, while an ongoing balloon dilation in FIG. 5B thereof, and after the balloon dilation FIG. 5C thereof.

Next, referring to FIG. 5, the inventor sets forth the analysis method of the blood flow amount at the narrow region 12 of the blood vessel 7a of the heart.

FIG. 5A, FIG. 5B, FIG. 5C are schematic image-views illustrating the narrow region 12 of the blood vessel 7a of the heart before a dilation (FIG. 5A) of the balloon 9 thereat, an ongoing dilation (FIG. 5B) of the balloon 9 thereat, and after the dilation (FIG. 5C) of the balloon 9 thereat. According to the aspect of the Embodiment 1, the image processing analysis element 4 implements the analysis while the balloon 9 is in place in the blood vessel 7a of the heart. In addition, the image processing analysis element 4 analyzes the blood flow respectively before and after the dilation of the blood vessel 7a with the balloon.

Referring to FIG. 5A, the balloon 9 is in place as if stepping over the narrow region 12 of the blood vessel 7a of the heart by the guide-wire 13 which is inserted by using the catheter. In such state, the contrast agent is administered through the catheter so that the blood flow before the dilation of the narrow region 12 of the blood vessel 7a of the heart is calculated. Next, referring to FIG. 5B, a liquid is administered into the balloon 9 to dilate the balloon 9 so that the narrow region 12 of the blood vessel 7a of the heart dilates. Then after, the blood flow is measured again after the liquid is removed from the balloon 9 and the balloon 9 is deflated. It is confirmed that the narrow region 12 of the blood vessel 7a of the heart is appropriately dilated (improvement level of the blood flow) by comparing the measured values before and after the dilation thereof. The blood flow can be measured while suspending the balloon in the blood vessel 7a, so that the balloon 9 can be immediately dilated to re-dilate the narrow region 12 of the blood vessel 7a of the heart when the dilation of the blood vessel 7a by the balloon 9 is insufficient.

(Method of X-ray Image Analysis)

Figure 6:
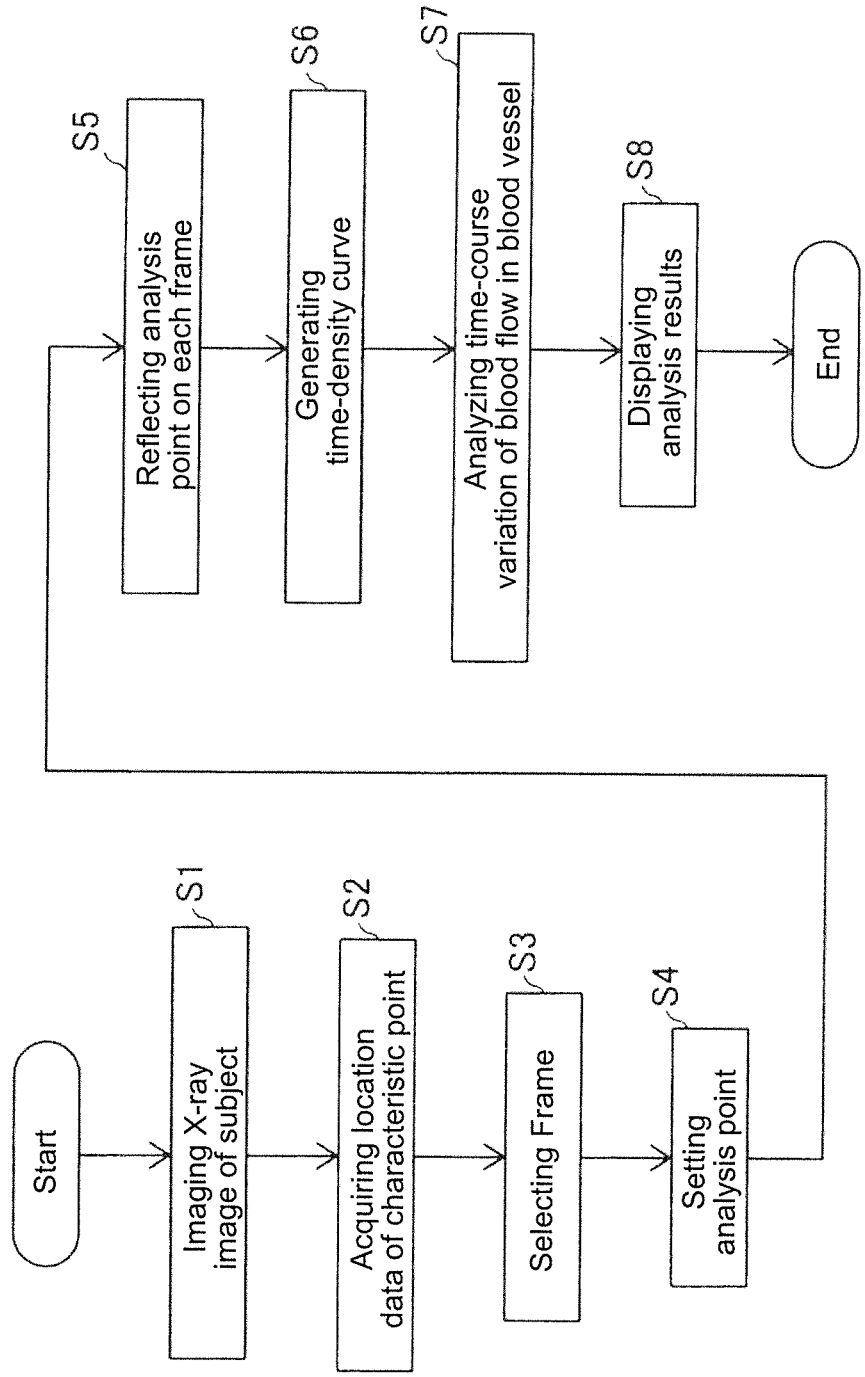
FIG. 6 is a flow-chart illustrating an X-ray imaging processing according to the alternative aspect of Embodiment 1 of the present invention.

Next, referring to FIG. 6, the inventor sets forth a method of an X-ray imaging analysis (X-ray in analysis processing) by using the X-ray imaging apparatus 100 according to the aspect of the Embodiment 1. In addition, the X-ray imaging analysis processing is executed by the image processing analysis element 4.

The X-ray image analysis method according to the aspect of the Embodiment 1 comprises the steps of acquiring location data relative to each frame 20 of characteristic points 10 of an X-ray image consisting of a plurality of the frames 20 that images a subject 7; reflecting an analysis point 11 on a blood vessel 7a in the X-ray image on each frame 20 based on each relative location between the characteristic point 10 of each frame 20 and the analysis point 11 that is set-up based on the location data of the characteristic point 10 every frame 20; and analyzing the time-course variation of the blood, flow in the blood vessel 7a based on the variation of the pixel values at the analysis point 11 of each frame 20 of the X-ray image.

Hereafter, the inventor specifically sets forth the method of the X-ray image analysis (X-ray image analysis processing).

At the step S1, an X-ray image of the subject 7 is taken. In detail, the X-ray image is taken while the balloon 9 is being introduced to the location stepping over the narrow region 12 of the blood vessel 7a Then, at the step S2, the characteristic point acquisition element 4a acquires location data of the characteristic point 10 relative to each frame 20. Then, the step proceeds to the step S3.

At the step S3, the input receiving element 4d receives the input of the selection operation by the user relative to the frame 20a that sets up the analysis point 11. Then, the step proceeds to the step S4. At the step S4, the analysis point setting element 4b sets up the analysis point 11 on the blood vessel 7a of the frame 20a selected by the user at the step S3. Then, the step proceeds to the step S5.

At the step S5, the analysis point setting element 4b reflects an analysis point 11 on a blood vessel 7a in the X-ray image on each frame 20 based on the respective relative locations between the location data of the characteristic point 10 relative to each frame 20 acquired at the step S2 and the analysis point 11 set up at the step S4. Then, the step proceeds to the step S6.

At the step S6, the image analysis element 4c acquires the time-density curve illustrated in the graph 21 (referring to FIG. 4) based on the time-course variation of the pixel values at the analysis point 11 relative to each frame 20 of the X-ray image. Then, the step proceeds to the step S7.

At the step S7, the image analysis element 4c analyzes the time-course variation of the blood flow in the blood vessel 7a from the graph 21 acquired at the step S6. Specifically, the rate of the blood flow and the amount thereof in the blood vessel 7a are calculated. Then, the step proceeds to the step S8.

At the step S8, the display 5 displays the analytical results. Any display method of the analytical results can be applied and for example, the numerical data of the rate of the blood flow and the amount thereof can be displayed, or a graph of the rate of the blood flow and the amount thereof can be displayed. Or the comparison value before and after dilation of the narrow region 12 can be displayed. Then, the X-ray image analysis processing (X-ray image analysis method) according to the aspect of the Embodiment 1 ends.

Effect According to the Aspect of the Embodiment 1

The following effects can be obtained according to the aspect of the Embodiment 1.

According to the aspect of the Embodiment 1, as set forth above, the X-ray imaging apparatus 100 comprises an X-ray irradiation element 1a that irradiates an X-ray to a subject 7; a FPD 2 that detects the X-ray that transmits through the subject 7; an X-ray image generation element 30 that generates an X-ray image of the subject 7 the image processing analysis element 4 that processes the X-ray image of the subject 7, and the image processing analysis element 4 reflects the analysis point 11 on each frame 20 based on the respective relative location between a characteristic point 10 of the X-ray image consisting of a plurality of frames 20 and an analysis point 11 set up based on the location data relative to the characteristic point 10 in each frame 20, and analyzes a time-course variation of the blood flow in a blood vessel 7a based on a variation of pixel values at the analysis point 11 in each frame 20 of the X-ray image. Accordingly, even when the location of the blood vessel 7a changes in between each frame 20 of the X-ray image of the subject 7, the analysis point 11 of each frame 20 can be set up on the basis of the characteristic point 10 that moves along with the blood vessel 7a, so that the time-course variation of the blood flow in the blood vessel 7a can be analyzed using the X-ray image. Consequently, the operator can comprehend the status of the blood flow in the blood vessel 7a using the X-ray image without using any additional device even relative to the region, such as a heart, where the blood vessel 7a moves, and in addition, and can cut the operation time and the radiation exposure thereby.

According to the aspect of the Embodiment 1, as set forth above, the image processing analysis element 4 comprises: the characteristic point acquisition element 4a that acquires location data of the characteristic point 10 relative to each frame 20 of the X-ray image; an analysis point setting element 4b that sets up the analysis point 10 on the blood vessel 7a in the X-ray image based on the location data of the characteristic point 10 every frame 20; and an image analysis element 4c that analyzes the time-course variation of the blood flow in the blood vessel 7a based on the variation of the pixel value at the analysis point 11 of each frame 20 of the X-ray image.

According to such aspect, the analysis point 11 on the blood vessel 7a in the X-ray image can be set up, so that an analysis of the time-course variation of the blood flow in the blood vessel 7a can be analyzed in further detail.

In addition, according to the aspect of the Embodiment 1, as set forth above, the image processing analysis element 4 calculates the rate of the blood flow and the amount thereof running, through the analysis point 11. According to such aspect, the rate of the blood flow and the amount thereof can be calculated from the X-ray image. Consequently, the rate of the blood flow and the amount thereof can be calculated without using an additional device such as the device implementing the Doppler method.

In addition, according to the aspect of the Embodiment 1, the image processing analysis element 4 further comprises an input receiving element 4d that receives the input from the user, and the image processing analysis element 4 sets up an analysis point in the frame 20a selected by the user based on the input from the user. According to such aspect, the analysis point 11 can be set up by reflecting the intention of the user, so that the analysis can be implemented along with the intention of the user.

In addition, according to the aspect of the Embodiment 1 as set forth above, the image processing analysis element 4 analyzes the blood flow in the blood vessel 7a of the heart. According to such aspect, the blood flow of the heart can be analyzed while beating continuously. As results, even when the blood vessel 7a of the heart is hard to be analyzed due to the vigorous movement thereof, such blood vessel 7a can be analyzed using the X-ray image without using any additional device. Now, the introduction of the additional device into the blood vessel takes more time and increases the radiation exposure. Therefore, according to the aspect of the present invention, it is effective that the introduction of such additional device is eliminated, so that the time needed fir the operation during a cardiovascular treatment can be cut and the radiation exposure can be reduced.

In addition, according to the aspect of the Embodiment 1, as set forth above, the image processing analysis element 4 implements the analysis while the balloon 9 is in place in the blood vessel 7a of the heart. Now, when the additional device is used to analyzes the blood flow, the balloon 9 and the device are exchanged respectively, so that an introduction of each and a removal thereof are needed, but in contrast, no additional device is needed according to the aspect of the present invention. As results, the number of the operation steps can be eliminated.

In addition, according to the aspect of the Embodiment 1, the image processing analysis element 4 analyzes the blood flow respectively before and after the dilation of the blood vessel 7a with the balloon 9. Now, when the additional device is used, the measurement of the blood flow and the dilation of the blood vessel 7a must be carried out with the additional device and the balloon 9 Specifically, when the additional device is used, the device applied to FFR device is introduced into the narrow region 12 of the blood vessel 7a to measure the blood flow. The balloon 9 is introduced into the narrow region of the blood vessel 7a to dilate the blood vessel 7a following the removal of the FFR device. The FFR device is reintroduced into the dilated region of the blood vessel 7a to measure the blood flow following the removal of the balloon 9. When the dilation of the blood vessel 7a is not satisfactory, it is necessary that the balloon 9 is removed and the FFR device is introduced into the narrow region 12 of the blood vessel 7a to measure the blood flow after the balloon 9 is reintroduced to dilate the blood vessel 7a and then removed therefrom. However, given the blood flow is respectively analyzed before and after the dilation of the blood vessel 7a with the balloon 9. no additional device is required to be introduced. In addition, for example, even when the blood vessel dilation is unsatisfactory with the balloon 9, the dilation of the blood vessel can be carried out again with the balloon 9 as is. Therefore, the operation time can be cut compared to the case when an additional device is used to analyze the blood flow. In addition, even when the blood vessel 7a is re-dilated, no balloon 9 is required to be re-introduced, so that the number of the X-ray irradiation due to introduction of the balloon 9 can be reduced. As results, the radiation exposure can be cut.

In addition, according to the aspect of the Embodiment 1, as set forth above, the method of the X-ray image analysis comprises the steps of; acquiring the location data at each frame 20 of the characteristic point 10 in the X-ray image consisting of a plurality of frames 20 that images the subject 7; reflecting the analysis point 11 in each frame 20 on the blood vessel 7a in the X-ray image based on each relative location between the characteristic point 10 in each frame 20 and the analysis point 11 set up based on location data relative to the characteristic point 10 every frames 20, and in addition, and analyzing the time-course variation of the blood flow in a blood vessel 7a based on a variation of images of an analysis point 11 in each frame 20 of the X-ray image. Accordingly, even when the location of the characteristic point 10 varies relative to each frame 20 of the X-ray image of the subject 7, the analysis point 11 in each frame 20 can be set up by the step of reflecting the analysis point 11 on the blood vessel 7a in the X-ray image on each frame 20.

In addition, the time-course variation of the blood flow in the blood vessel 7a can be analyzed by the step of analyzing the time-course variation of the blood flow in the blood vessel 7a. Consequently, the X-ray image analysis method can be provided, by which the operator can comprehend the status of the blood flow in the blood vessel 7a in the X-ray image without using any additional device even relative to the region, such as a heart, where the blood vessel 7a moves, and in addition, can cut the operation time and the radiation exposure.

Embodiment 2

Figure 7:
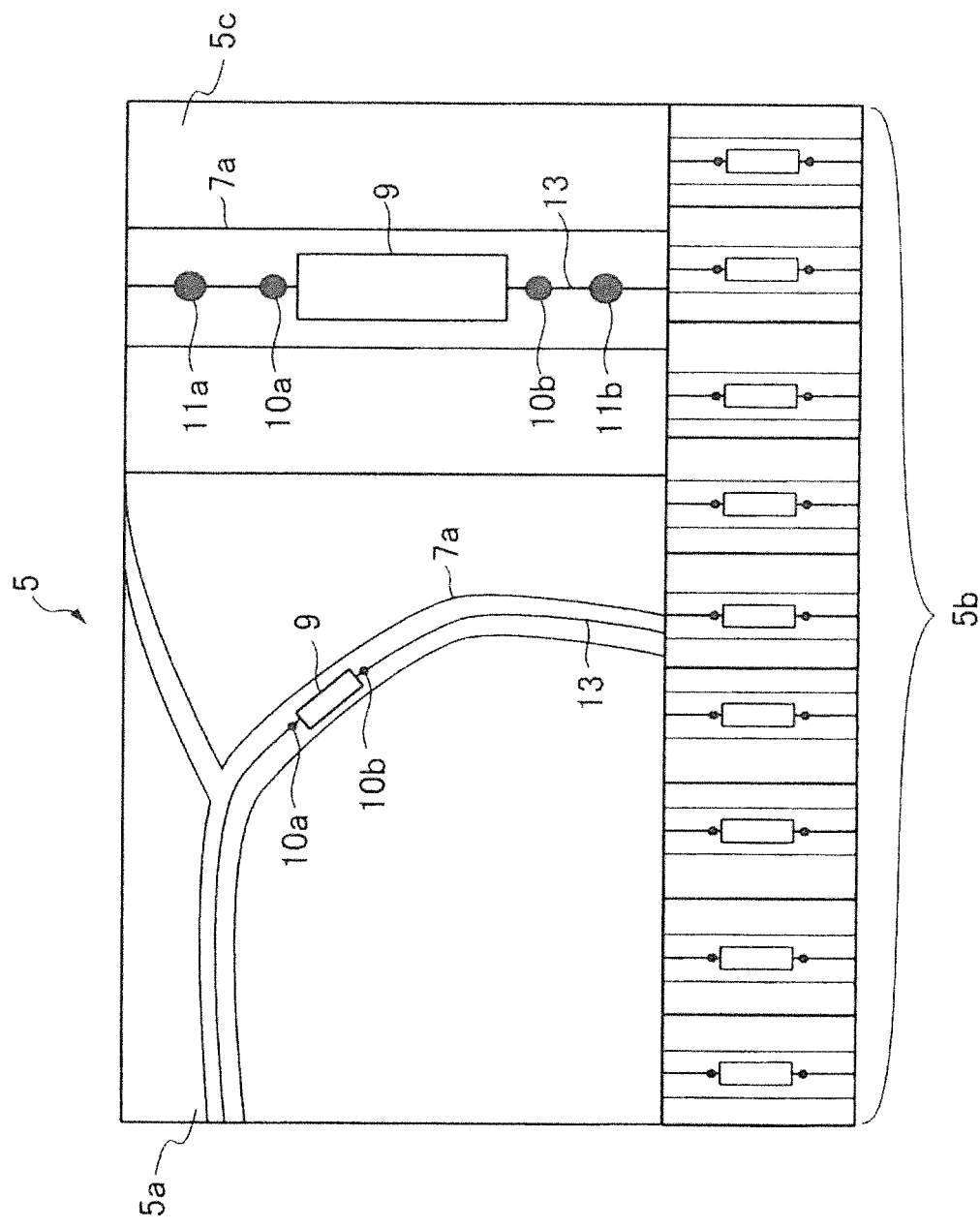
FIG. 7 is a schematic view illustrating a display of the display element and a method that sets up the analysis point of the X-ray imaging apparatus according to the aspect of Embodiment 2 of the present invention.

Next, referring to FIG. 1, FIG. 2, and FIG. 7, the inventor sets forth an operation of the X-ray imaging apparatus 200 according to the aspect of the Embodiment 2 of the present invention. According to the aspect of the Embodiment 2, the analysis point 11 is set up based on the input from the user in a characteristic point image 5c (referring to FIG. 7) that fixes the characteristic point 10 that is output in order as a video-image, so that it is different from the aspect of the Embodiment 1 set forth above, in which the user selects the frame 20a to set up the analysis point 11 from a plurality of the frames 20 in the X-ray image of the subject 7. In addition, the same element as illustrated above according to the aspect of the Embodiment 1 is not set forth while providing the identical reference sign in FIGS.

Referring to FIG. 1. FIG. 2, according to the aspect of the Embodiment 2, with regard to the X-ray imaging apparatus, the image processing analysis element 41 further comprises an input receiving element 4d that receives the input from the user as well as the aspect of the Embodiment 1. In addition, FIG. 7 is a schematic image view illustrating a display of the display element 5 of the X-ray imaging apparatus 200 according to the aspect of the Embodiment 2. Referring to FIG. 7, the image processing analysis element 41 cuts out each frame 5b of the live video-image 5a of the X-ray images, which is continuously acquired based on the characteristic point 10; video-outputs the characteristic point images 5c, of which location is fixed on the basis of the characteristic point 10, in order, and sets up an analysis point 11 based on the input from the user in the characteristic point image 5c, In addition, the patent document, JP2010-131371, discloses the method to display the real-time image in which the location is aligned by detecting the location of the characteristic point of the target subject and aligning the location to the characteristic point of the base image of the past frame; and the same method is applied to the aspect of the present Embodiment, so that the method that fixes the location based on the characteristic point 10 is not set forth.

According to the aspect of the Embodiment 2, the display element 5 displays the live video-image 5a of the X-ray images output as a video-image in order by the image processing analysis element 41; each frame 5b of the X-ray images; and characteristic point image 5c, which is cut out from each frame 5b of the X-ray images that are continuously acquired based on the characteristic point 10, and the location thereof is fixed on the basis of the characteristic point 10 on the same screen page.

Specifically, according to the aspect of the Embodiment 2, the image processing analysis element 41 cuts out the portion displaying the characteristic point 10 from each frame 5b of the X-ray images acquired continuously; aligns the locations of the characteristic points 10, which are different in each frame 5b; and generates the characteristic point image 5c to be displayed, in which the location of the characteristic point 10 is fixed. The image processing analysis element 41 video-outputs the live video-images 5a of the X-ray images, each frame 5b of the X-ray images, and the characteristic point image 5c to the display element 5 in order. The display element 5 displays the live video-images 5a of the X-ray images, each frame 5b of the X-ray images, and the characteristic point image 5c in the same screen page.

In addition, the image processing analysis element 41 sets up an analysis point 11 in the characteristic point image 5c based on the input from the user. Specifically, the image processing analysis element 41 sets up the analysis point 11 in the characteristic point image 5c based on the data of the analysis point 11, which is received by the input-receiving element 4d and input from the user.

X-Ray Image Analysis Method According to the Aspect of the Embodiment 2

Figure 8:
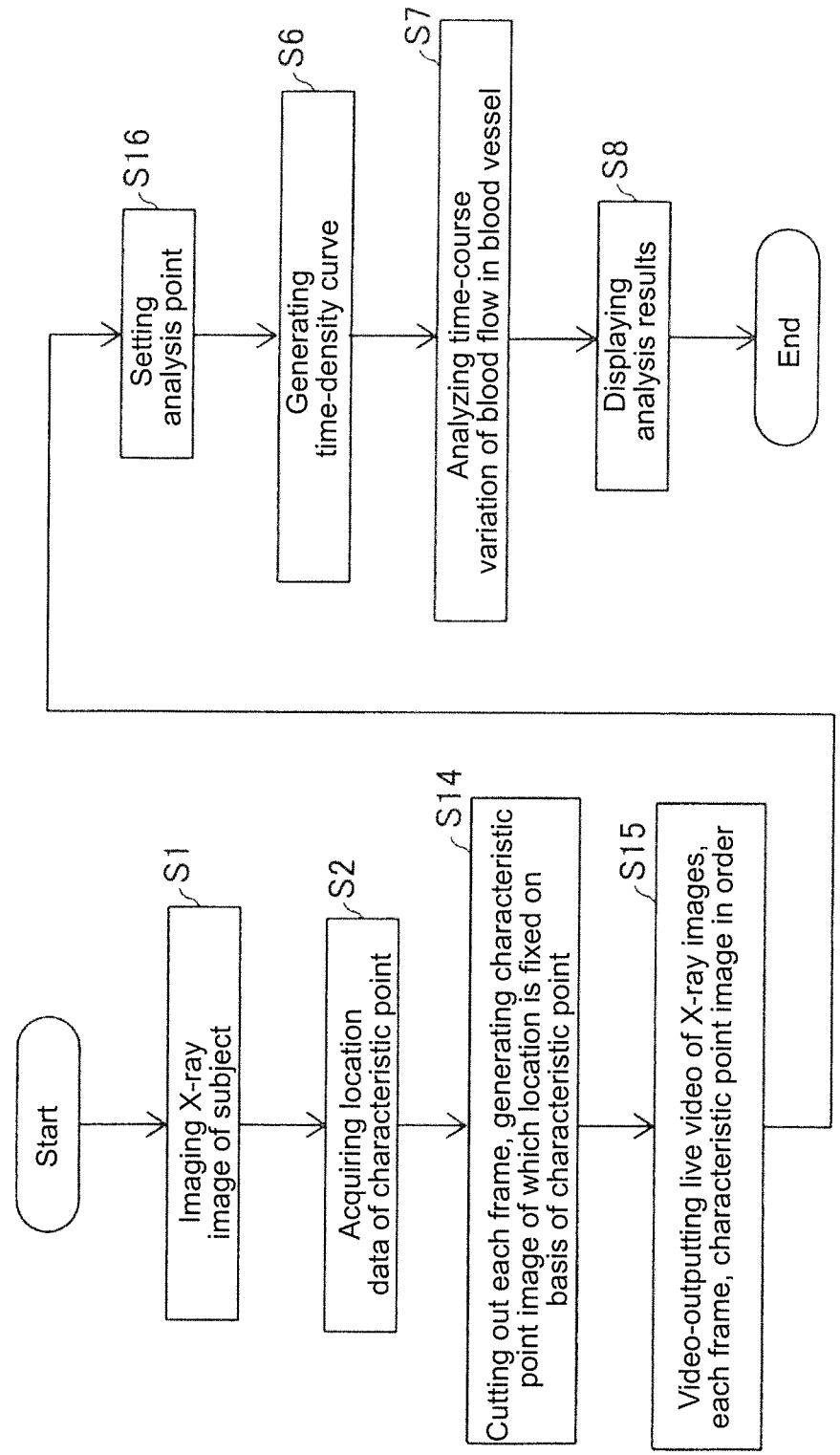
FIG. 8 is a flow-chart illustrating an image processing according to the aspect of Embodiment 2 of the present invention.

Next, referring to FIG. 8, the inventor sets forth a method of an X-ray imaging analysis (X-ray imaging analysis processing) by using the X-ray imaging apparatus 200 according to the aspect of the Embodiment 2. The X-ray imaging analysis processing is executed by the image processing analysis element 41. In addition, the same step as the step in the Embodiment 1 is not set forth and the inventor sets forth only the step different from the step according to the aspect of the Embodiment 1.

As well as the Embodiment 1, the step S1, S2 are carried out and then the step S14 is carried out. At the step S14, the image processing analysis element 41 cuts out each frame 5b and generates the characteristic point image 5c of which location is fixed on the basis of the characteristic point 10. Then, at the step S15, the live video-images 5a of the X-ray images, each frame 5b and the characteristic point image 5c are video-output in order. Then, the step proceeds to the step S16.

At the step S16, the input receiving element 4d receives the data of the analysis point 11 that is input from the user. And, the analysis point setting element 4b sets, up the analysis element 11 in the characteristic point image 5c based on the data of the analysis point 11 received by the input-receiving element 4d. Then, the steps proceed to the step S6, S7, S8 and then, the X-ray image analysis processing (X-ray image analysis method) according to the aspect of the Embodiment 2 ends.

Effect According to the Aspect of the Embodiment 2

The following effect can be obtained according to the aspect of the Embodiment 2.

According to the aspect of the Embodiment 2, as set forth above, the image processing analysis element 41 comprises an input receiving element 4d that receives an input from the user, and the image processing analysis element 41 cuts out each frame 5b of the live video-image 5a of the X-ray images, which is continuously acquired based on the characteristic point 10; video-outputs the characteristic point images 5c, of which location is fixed on the basis of the characteristic point 10, in order, and sets up an at point 11 based on the input from the user in the characteristic point image 5c, According to such aspect, the analysis point 11 can be set up using the video-image, in which the characteristic point 10 displayed in real time without searching a frame that facilitates to make sure the characteristic point 10, when the analysis point 11 is set up.

In addition, other effects according to the aspect of the Embodiment 2 is the same as the aspect of the Embodiment 1.

Embodiment 3

Figure 9:
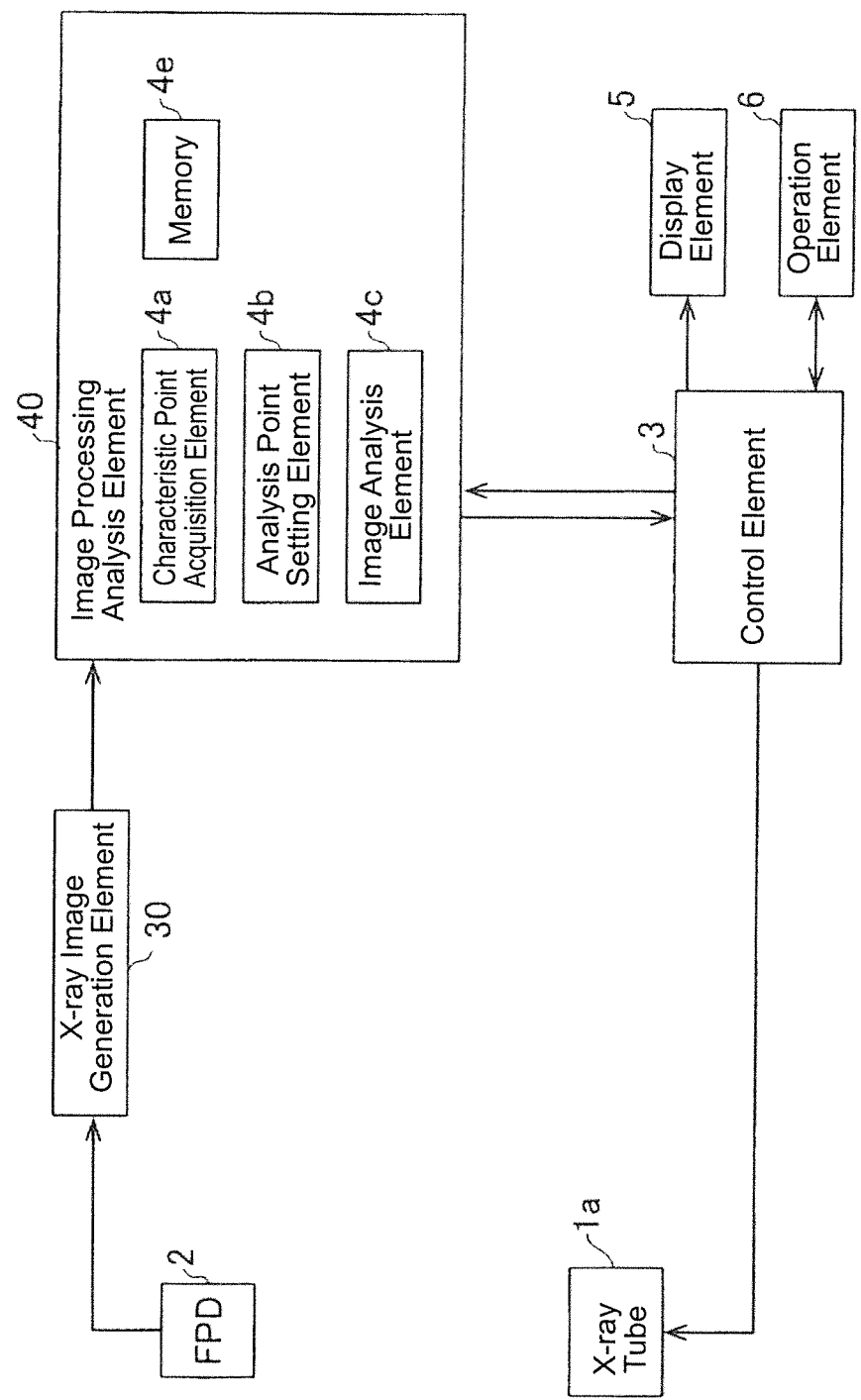
FIG. 9 is a block view illustrating the entire structure of the X-ray imaging apparatus according to the aspect of Embodiment 3 of the present invention.
Figure 10:
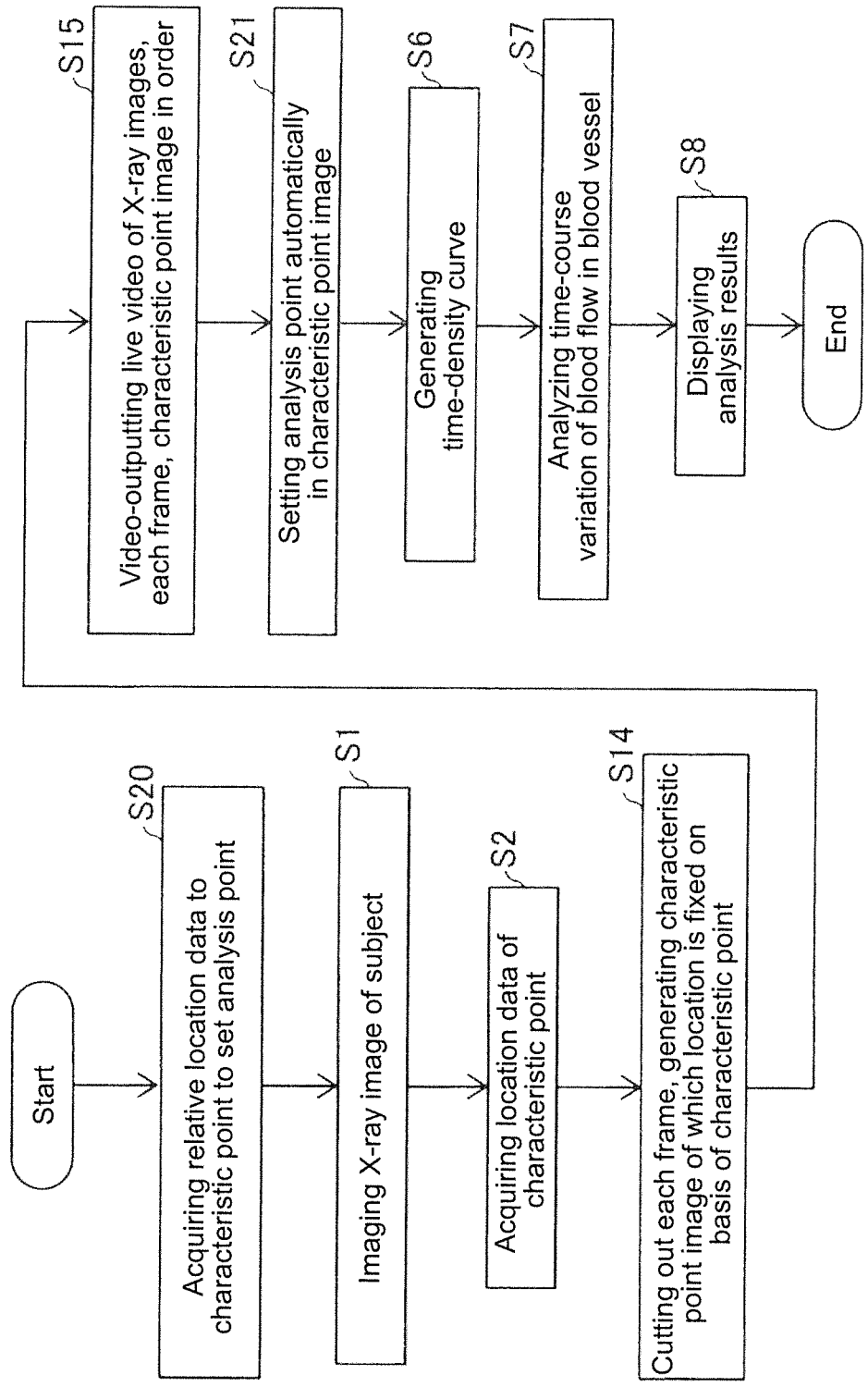
FIG. 10 is a flow-chart illustrating an image processing according of the X-ray imaging apparatus according to the aspect of the Embodiment 3 of the present invention.

Next, referring to FIG. 1, FIG. 9 and FIG. 10, the inventor sets forth an operation of the X-ray imaging apparatus 300 according to the aspect of the Embodiment 3. According to the aspect of the Embodiment 3, the image processing analysis element 42 sets up the analysis point 11 to the predetermined location set up by the user in advance, so that it is different from the aspects of the Embodiment 1, 2, in which the analysis point 11 is set up based on the input from the user. Specifically, the analysis point 11 is automatically set up without receiving an input from the user relative to the analysis point 11. In addition, the same element as illustrated above according to the aspects of the Embodiment 1, 2 is not set forth while providing the identical reference sign in FIGS.

Referring to FIG. 1, the X-ray imaging apparatus 300 comprises an image processing analysis element 42. Referring to FIG. 9, in detail, according to the aspect of the Embodiment 3, the image processing analysis element 42 comprises a characteristic point acquisition element 4a, an analysis point setting element 4b, an image analysis element 4c, and a memory 4e. The relative location data between the characteristic point 10 and the analysis point 11, which are input from a user are stored in the memory 4e. The relative location data can be set up, e.g., as is 2 mm on the extended line of the straight line connecting between the two points of the characteristic points 10 (characteristic point 10a and 10b).

Now, according to the aspect of the Embodiment 3, the image processing analysis element 42 sets up the analysis point 11 to the predetermined location acquired based on the coordinate of the characteristic point 10. In detail, when the characteristic point image 5c is generated, the analysis point 11 is set up on the characteristic point image 5c based on the relative location date between the characteristic point 10 and the analysis point 11, which are stored in the memory 4e.

X-ray Image Analysis Method According to the Aspect of the Embodiment 3

Next, referring to FIG. 10, the inventor sets forth a method of an X-ray imaging analysis (X-ray imaging analysis processing) by using the X-ray imaging apparatus 300 according to the aspect of the Embodiment 3. The X-ray image analysis processing is executed by the image processing analysis element 42. In addition, the same step as the step in the Embodiment 1, 2 is not set forth and the inventor sets forth only the step different from the step according to the aspect of the Embodiment 1, 2.

At the step S20, the relative location data between the characteristic point 10 and the analysis point 11 to set up the predetermined location of the analysis point 11 input from the user are stored in the memory 4e. Then, the steps S1, S2, S14, S15 are carried out and then the step S21 is carried out.

At the step S21, the analysis point 11 is automatically set up by the analysis point setting element 4b based on the relative location data between the characteristic point 10 and the analysis point 11, which are stored in the memory 4e, and the coordinate of the characteristic point 10. Then, the steps proceed to the step S6, S7. S8 and then, the X-ray image analysis processing (X-ray image analysis processing method) according to the aspect of the Embodiment 3 ends.

Effect According to the Aspect of the Embodiment 3

The following effect can be obtained according to the aspect of the Embodiment 3.

Now, according to the aspect of the Embodiment 3, the image processing analysis element 42 sets up the analysis point 11 to the predetermined location acquired based on the coordinate of the characteristic point 10. According to such aspect, the analysis point can be automatically set up without an input from a user, so that the usability can be improved.

In addition, other effects according to the aspect of the Embodiment 3 are the same as the aspect of the Embodiment 1.

Alternative Embodiment

In addition, the aspects of the Embodiments disclosed at this time are examples and not limited thereto in any points. The scope of the present invention specified in the claims but not in the above description of the aspect of the Embodiments and all alternative (alternative examples) are included in the scope of the claims and equivalents thereof.

Further, according to the aspect of the Embodiments 1 to 3 set forth above, the example, in which the blood flow of the blood vessel 7a of the heart is analyzed, is illustrated, but the present invention is not limited thereto. According to the present invention, other regions, e.g., a chest of the subject 7 and so forth, than the blood vessel 7a of the heart can be subject to the X-ray imaging as long as the imaging target moves.

Further, according to the aspect of the Embodiments 1 to 3 set forth above, the example of the human body is illustrated for imaging, but the present invention is not limited thereto. According to the present invention, the X-ray imaging apparatus can be applied to other animals (dog, mouse) than a human.

Further, according to the aspect of the Embodiments 1 to 3 set forth above, the example, in which two analysis points 11 are set up, is illustrated, but the present invention is not limited thereto. For example, more than three analysis points can be set up.

Given the number of the analysis points 11 increases, the accuracy level of the analysis of the blood flow can be improved. In addition, given the analysis point 11 is set up in the region including the analysis points 11a, 11b, just one analysis point 11 can be applied to be set up.

Further, according to the aspect of the Embodiment 1 set forth above, the example, in which the rate and amount of the blood flow, is illustrated, but the present invention is not limited thereto. At least one of the blood flow rate at the analysis point and the blood flow amount thereat can be calculated.

Further, according to the aspect of the Embodiments 1 to 3 set forth above, the example, in which the time-density curve is applied to analyze the blood flow of the blood vessel 7a, is illustrated, but the present invention is not limited thereto. The blood flow of the blood vessel 7a can be analyzed using, a method other than the method of the time-density curve.

Further, according to the aspect of the Embodiments 1 to 3 set forth above, the example, in which the X-ray imaging apparatus is hanged from the ceiling, is illustrated, but the present invention is not limited thereto. The aspect of the present invention can be applied to the floor-type X-ray imaging apparatus.

Those of skill would further appreciate that the various illustrative logical elements, blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (ED), laser disc, optical disc, digital versatile disc (DVD), floppy disk and Blu-ray® disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

The computers described herein may be any kind of computer having at least one processor, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGNS

1a X-ray source
2 FPD (X-ray detection element)
2a X-ray image generation element
4, 41, 42 Image processing analysis element
4a Candidate point acquisition element
4b Analysis point setting element
4c Image analysis element
4d Input receiving element
5c Characteristic point image
7a Heart vessel
9 Balloon
10 (10a, 10b) Characteristic point
11 (11a, 11b) Analysis point
20 A plurality of images taking an X-ray subject
20a Frame selected by a user

What is claimed is:

1. An X-ray imaging apparatus, comprising:
an X-ray irradiator that irradiates an X-ray to a subject;
a detector that detects the X-ray that transmits through said subject;
an X-ray image generator that generates an X-ray image consisting of a plurality of frames including a physical marker installed to a device inserted in a blood vessel of said subject obtained by imaging said subject; and
a processor that processes the X-ray image of said subject; and
a storage device that stores data received from said processor;
wherein said processor, further comprises:
a physical marker location specifying portion that specifies a location of said physical marker for each of said plurality of frames including said physical marker inserted in said blood vessel of said subject;
a first analysis point setting portion that sets an analysis point in a first frame of said plurality of frames;
a calculator that calculates a relative location data including an angle between a line connecting a location of said physical marker and a location of said analysis point in said first frame and a line connecting a front end and a rear end of said device, and a first distance between said location of said physical marker and said location of said analysis point in said first frame;
a storage controller that stores said relative location data in said storage device;
a second analysis point setting portion that sets a location of said analysis point in a second frame of said plurality of frames, said location of said analysis point in said second frame having both a same angle as said angle and a same second distance as said first distance, a same relative location as said relative location of said analysis point to said physical marker in said first frame, with respect to a location of said physical marker in said second frame, based on said location of said physical marker in said second frame and said relative location data stored in said storage device;
an analyzer that analyzes data regarding a blood flow based on a time-course variation of pixel values at said analysis point in said first frame and said analysis point in said second frame.

2. The X-ray imaging apparatus, according to the claim 1, wherein:
said processor calculates at least one of a rate of said blood flow and an amount thereof, running at said analysis point in said first frame and said analysis point in said second frame.

3. The X-ray imaging apparatus, according to the claim 1, wherein:
said processor, further comprises:

an input receiving portion that receives an input from a user, and said processor sets up said analysis point in said first frame that is selected by the user, based on the input from the user.

4. The X-ray imaging apparatus, according to the claim 1, wherein:
said processor receives an input from a user, and
said processor cuts out each said frame of said X-ray image that is continuously acquired based on said physical marker; video-outputs each said frame, in which locations of said physical markers in each frame are aligned; and sets up said analysis point in said first frame based on an input from a user.

5. The X-ray imaging apparatus, according to the claim 1, wherein:
said processor analyzes said blood flow in said blood vessel of a heart.

6. The X-ray imaging apparatus, according to the claim 5, wherein:
said processor implements an analysis while a balloon is in place in said blood vessel of said heart.

7. The X-ray imaging apparatus, according to the claim 6, wherein:
said processor analyzes said blood flow respectively before and after a dilation of said blood vessel with said balloon.

8. An X-ray image analysis method, comprising the steps of:
inserting a physical marker installed on a device into a blood vessel of a subject;
specifying a location of said physical marker for each of a plurality of frames including said physical marker installed to said device inserted in said blood vessel of said subject in the X-ray image including said plurality of frames obtained by imaging said subject;
setting an analysis point in a first frame of said plurality of frames;
calculating a relative location data including an angle between a line connecting a location of said physical marker and a location of said analysis point in said first frame and a line connecting a front end and a rear end of said device, and a first distance between said location of said physical marker and said location of said analysis point in said first frame;
setting a location of said analysis point in a second frame of said plurality of frames, said location of said analysis point in said second frame having both a same angle as said angle and a same second distance as said first distance, a same relative location as said relative location in said analysis point to said physical marker in said first frame, with respect to a location of said physical marker in said second frame, based on said location of said physical marker in said second frame and said relative location data; and
analyzing data regarding a blood flow based on a time-course variation of pixel values at said analysis point in said first frame and said analysis point in said second frame.

* * * * *